US00PP18600P3

(12) United States Plant Patent
Tous

(10) Patent No.: US PP18,600 P3
(45) Date of Patent: Mar. 18, 2008

(54) OLIVE TREE 'ARBEQUINA OLINT'

(50) Latin Name: *Olea europaea*
Varietal Denomination: Arbequina OLINT

(76) Inventor: Joan Tous, 618 E. Gridley Rd., Gridley, CA (US) 95948

( * ) Notice: Subject to any disclaimer, the term of this patent is extended or adjusted under 35 U.S.C. 154(b) by 0 days.

(21) Appl. No.: 11/093,398

(22) Filed: Mar. 29, 2005

(65) Prior Publication Data

US 2006/0225168 P1 Oct. 5, 2006

(51) Int. Cl.
*A01H 5/00* (2006.01)

(52) U.S. Cl. ..... Plt./158
(58) Field of Classification Search ..... Plt./158
See application file for complete search history.

(56) References Cited

U.S. PATENT DOCUMENTS

| | | | |
|---|---|---|---|
| PP5,829 | P | 12/1986 | Haas |
| PP7,750 | P | 12/1991 | Zampini |
| PP10,641 | P | 10/1998 | Sonnoli, Jr. |
| PP13,077 | P2 | 10/2002 | Fontanazza |

OTHER PUBLICATIONS

Tous et al. "IRTA–i–18": A Clone of the "Arbequina" Olive Variety, Olivae, No. 77, Jun. 1999, pp. 50–52.*
California Olive Oil News, vol. 5, Issue 7, Jul. 2002 [online], [retrieved on Dec. 5, 2005]. Retrieved from the Internet <http://www.oliveoilsource.com/newsletter/olivenews5–7.htm> pp. 1–10.*
IRTA, The Arbequina Irta–i–18 Olive Clone [online], [retrieved on Apr. 18, 2006]. Retrieved from the Internet <http://www.irta.es/eng/index.html>, 5 pages.*
Garden Web Glossary of Botanical Terms [online], retrieved on Dec. 20, 2006}. Retrieved from the Internet <http://glossary.gardenweb.com/glossary/> 3 pages.*
The New Royal Horticultural Society Dictionary of Gardening, 1992, vol. 3, p. 354.*

* cited by examiner

*Primary Examiner*—Kent Bell
*Assistant Examiner*—June Hwu
(74) *Attorney, Agent, or Firm*—Mark D. Miller

(57) ABSTRACT

This new invention of an olive tree is characterized by its similarity to the 'Arbequina Standard' from which it is a clonal selection (naturally occurring mutation) from which it is distinguished by higher productivity, larger fruit size, better pulp to stone ratio, higher oil yield, and better oil quality. The plants are ideally suited for mechanical harvesting and high density planting. The fruit matures in northern California during the first week of October.

4 Drawing Sheets

Olive tree: (*Olea europaea*).

BACKGROUND OF THE NEW VARIETY

The present invention relates to a new and distinct variety of olive plant, *Olea europaea,* and will hereafter be denominated varietally as 'Arbequina OLINT' and more particularly to an olive plant that produces fruit for harvest during the first week of October in the Gridley area of the northern Sacramento Valley in California and which is further distinguished as to novelty by producing a fruit with higher productivity than the parent 'Arbequina Standard' variety from which it is a clonal selection (naturally occurring mutation). The maturing date in Northern California is different than in Spain but is materially the same with better oil quality.

ORIGIN AND ASEXUAL REPRODUCTION OF THE NEW VARIETY

The 'Arbequina OLINT' was originally selected from 110 individual trees from olive orchards across Spain for possessing superior traits in 1986. Four years later, fifteen (15) advanced further selections were made that possessed superior production and uniformity in ripening. Two years later, these advanced selections were propagated vegetatively (asexually reproduced) and placed in replicated trials. In 1997, the new variety evaluation provided the information on its superior traits over the 'Arbequina Standard.' The new invention was imported into Oregon, USA where it was grown and then vegetatively propagated by rooted cuttings and shipped to Gridley, Calif. in 2001. Over the past three years propagational trees were provided as rooted cuttings. The trees are stable and reproduce true to type in successive generations of asexual reproduction. The fruit produced by these vegetatively propagated trees are in all respects identical to the parent.

SUMMARY OF THE NEW VARIETY

This new variety of olive tree is characterized by having the general characteristics of the 'Arbequina Standard' variety with several differences including: semi-erect tree (rather than open), a different branching pattern in which the branching occurs higher up on the trunk, is more upright, and promotes higher production, fruit has smaller pits, higher oil content and larger fruit. Due to the semi-erect structure and size of this olive tree, it is well suited for mechanical harvesting and high density planting (i.e., 670 plants/acre).

DETAILED DESCRIPTION

Figure 1:
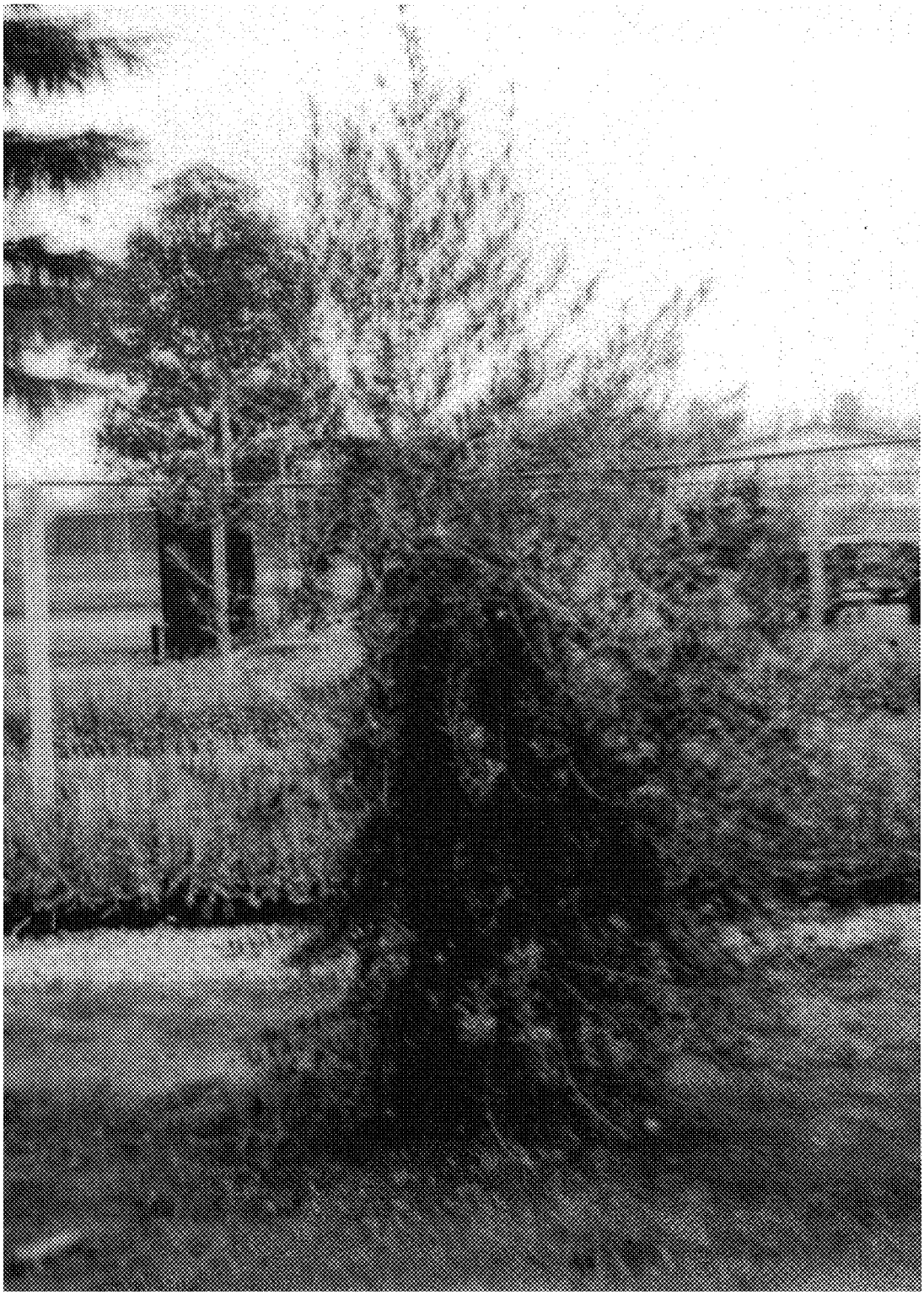
FIG. 1 is a color photograph of the olive tree at third leaf (three years old) displaying it semi-erect in appearance.
Figure 2:
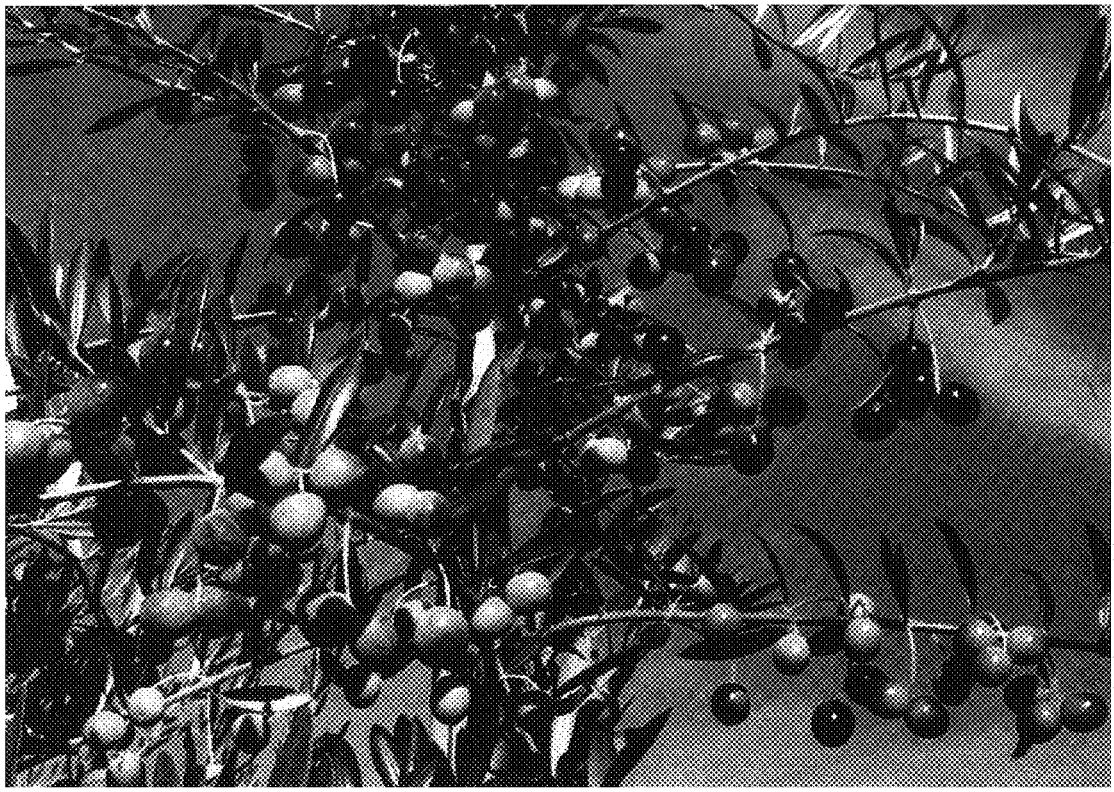
FIG. 2 is a color photograph of the new invention showing it in the third leaf.
Figure 3:
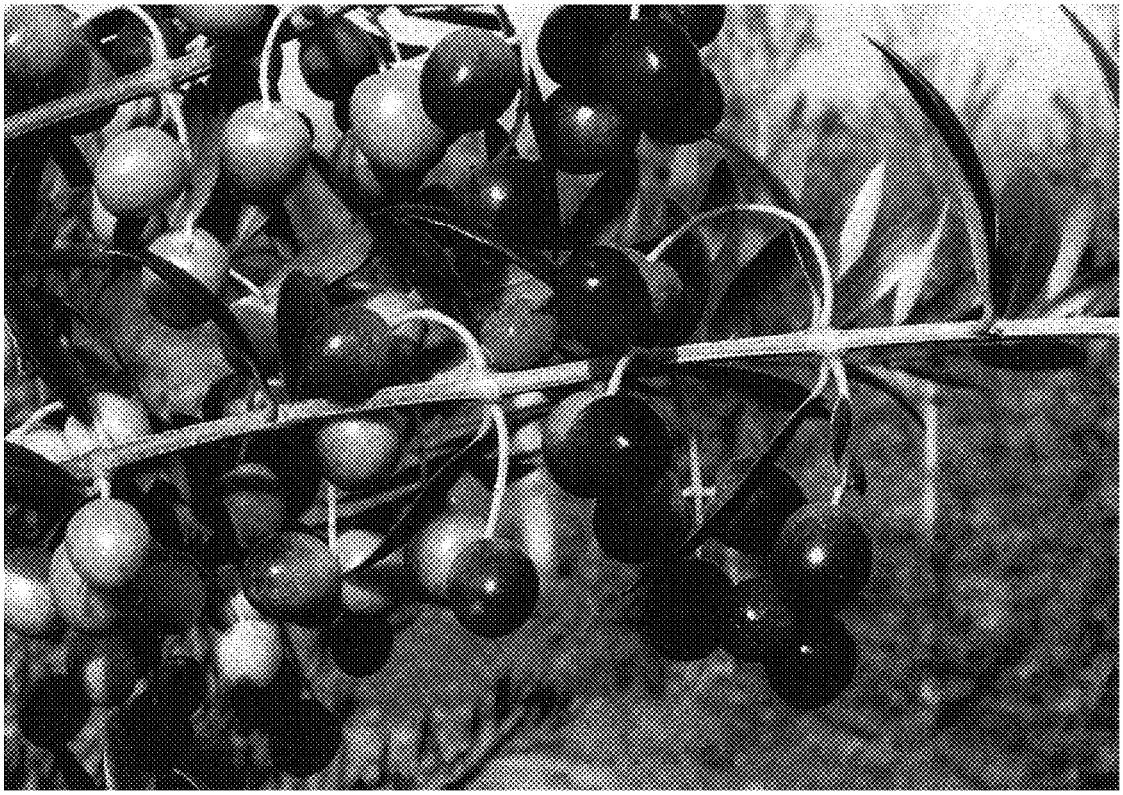
FIG. 3 is a color photograph showing a display of the fruit clusters, twigs and branches.
Figure 4:
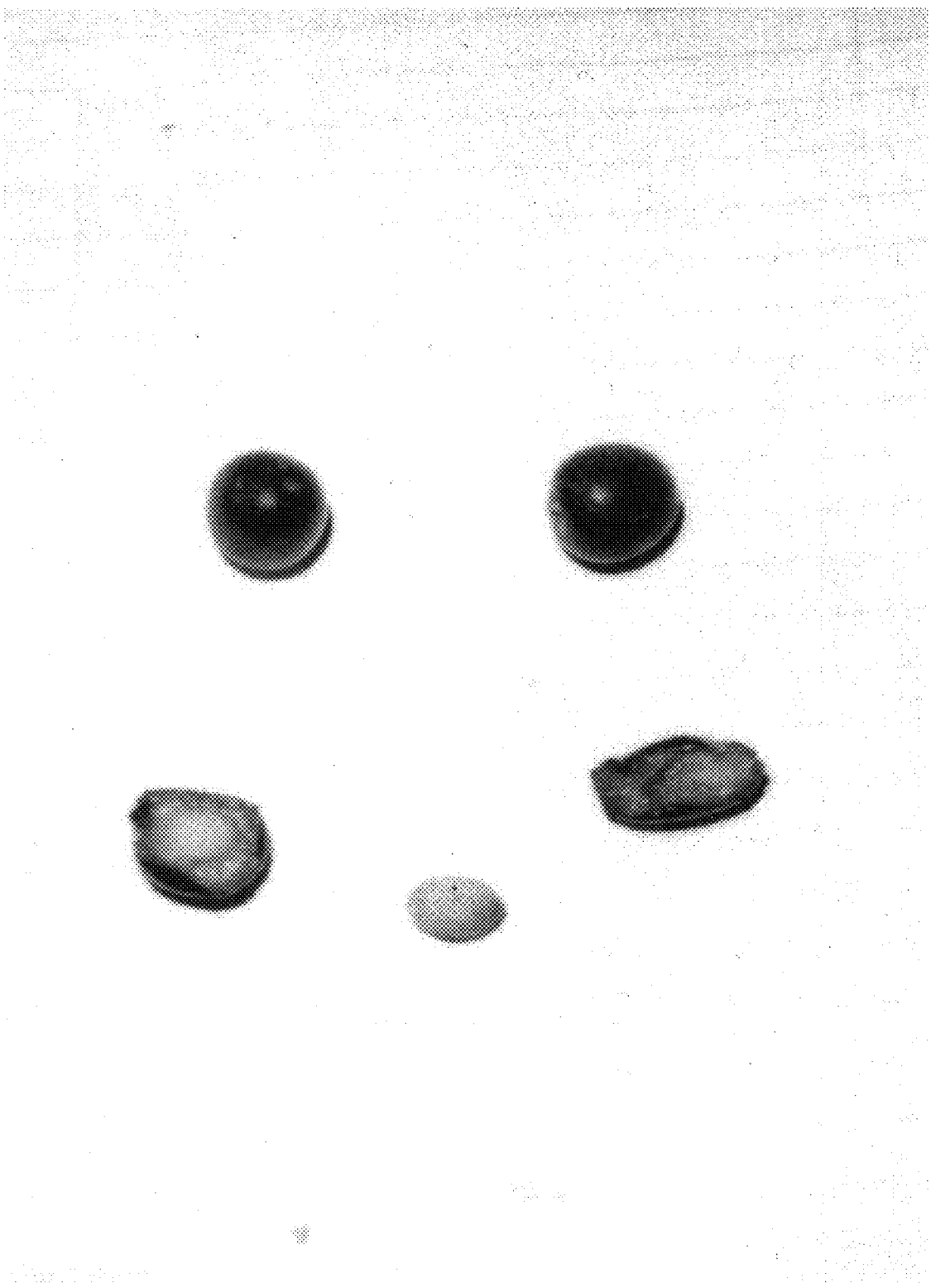
FIG. 4 is a color photograph showing two whole fruits displaying the shape of the fruit (top), a fruit cut in half with seed in place (lower left), another fruit cut in half displaying the flesh and pit well (lower right), and a seed in dry state (lower center).

Referring more specifically to the horticultural details of the new and distinct variety of olive trees, the following descriptions have been observed in 5-year old trees under the ecological details prevailing at the site of origin which is located near Gridley, Calif. in the Sacramento Valley of Northern California. All major color designations are by reference to the Dictionary of color by Maerz & Paul, First Edition, 1930. Common colors are also employed.

TREE

Size: Small, semi-erect.
- *Height.*—9–10 feet (274–305 cm.).
- *Width.*—2–3½ feet (61–107 cm.).

Vigor: Medium, good.
Chilling requirements: Normal for olives.
Shape: Upright, semi-erect.
Productivity: The production pattern and level is uniform and continuous, producing fruit with generally identical shape, color and oil production.
Regularity of bearing: Regular.

TRUNK

Size: Circumference of 6 inches (15 cm), 11 inches (28 cm) above ground.
Surface texture: Smooth.
Color: Plumbago Grey (44-B-4).
Lenticels: Number: few; scattered, irregularly spaced; Size: very small.

BRANCHES

Size: Small, circumference of 2–3 inches (5–8 cm), 15 inches (38 cm) above crotch.
Surface texture:
- *Mature.*—Smooth.
- *Immature.*—Smooth.

Color of branches one year or older: Grey Drab, Quaker Grey (1-B-1).
Color of branches less than one year old (immature): Light Grey (36-A-1).
Lenticels:
- *Numbers.*—Few and scattered.
- *Size.*—Very small.

LEAVES

Configuration: Leaves on opposite side of the stem.
Size: Small.
- *Length.*—45–49 mm (1.76–1.91 in.).
- *Width.*—10–12 mm (0.39–0.47 inch).

Shape: Lancelate.
Color:
- *Upwardly disposed surface.*—Fir (glossy) (24-E-7).
- *Downwardly disposed surface.*—Cosse Green (19-L-5).

Marginal form: Entire (smooth), without teeth or lobes.
Apex: Narrowly acute.
Base: Cuneate.
Surface texture:
- *Upwardly disposed surface.*—Smooth.
- *Downwardly disposed surface.*—Smooth, slightly pubescent.

Leaf vein:
- *Color.*—Chrysolite Green (19-K-3).
- *Thickness.*—Less than 1 mm (0.039 in.).

Glandular characteristics: None.
Petiole:
- *Size.*—Medium.
- *Length.*—4–6 mm (0.16–0.23 in.).
- *Thickness.*—1.5 mm (0.06 in.) in diameter.
- *Color.*—Palm Leaf (14-L-1).

Stem glands: None.
Stipules: None.
Flower buds: Small.
- *Surface texture.*—Slightly pubescent.

FLOWERS

Date of first bloom: Mid May to end of May.
Size: Small, 4–6 mm (0.16 in.–0.24 in.).
- *Petals.*—Color: White.

Average bud size: Small, 1–2 mm (0.04–0.079 inch).
Number of florets per inflorescence: 9–15.
Number of sepals: 4.
Number of petals: 4.
Fragrance: Very mild.
Reproductive organs: 1 pistil; 15–25 stamens.
Pollen color: Yellow, Empire Y. (9-K-3).

FRUIT

Date of maturity: First week of October, in clusters of 2–3.
Size: Small, 2.85 grams.
- *Diameter.*—14–15 mm (0.55–0.59 in.).
- *Length.*—16–18 mm (0.62–0.70 in.).

Shape: Elliptical.
Form:
- *Uniformity.*—Good.
- *Symmetrical or asymmetric.*—Slightly asymmetrical.
- *Suture.*—None.
- *Stem cavity.*—Width: 6 mm (0.23 in.). Depth: 3 mm (0.12 in.). Length: 10 mm (0.39 in.).

Stem: Short 2–3 mm (0.08–0.12 in.).
Caliper: 1.5 mm (0.06 in.).
Apex: Rounded.
Pitsil point: Rounded.
Skin:
- *Thickness.*—Thin.
- *Texture.*—Smooth.
- *Immature fruit color.*—Jonquil (9-J-5).
- *Mature fruit color.*—From Byzantium (44-K-7) to Kurdistan (48-A-10).
- *Flesh color.*—Tinsel Deepstone (13-L-7).
- *Color of surface of pit cavity.*—Sudan (13-E-4).
- *Color of pit well.*—Sudan (13-E-4).

Juice production: Very good.
Flavor: Very good.
Aroma: None.
Texture: Smooth, firm.
Fibers: Few.

Ripening: Even.

Eating quality: Used for oil production and in some cases for canning.

SEED

Free or cling: Cling.

Fibers: Few.

Size:

*Length.*—12 mm (0.47 inch).

*Width.*—7 mm (0.28 inch).

*Thickness.*—5 mm (0.20 inch).

Form: Elliptical.

Surface texture: Nearly smooth, hard.

Apex shape: Rounded with a point.

*Color* (*dry*).—Peruvian Brown (13-L-11).

Base: Rounded.

Sides: Slightly asymmetrical.

Ridges: Not uniform.

Tendency to split: None known.

Use: Olive oil production and in some cases for canning.

Keeping and shipping quality: Good.

Harvesting: First week of October.

Chemical Analysis (Characteristics)

'Arbequina OLINT'

TABLE 1

Virgin Oil Fatty Acid Percentage

| Type of Fatty Acid | Percent of Total Oil Content |
|---|---|
| C16:0 Palmitic Acid | 16.0 |
| C16:1 Palmitoleic Acid | 1.4 |
| C18:0 Esteric Acid | 1.5 |
| C18:1 Oleic Acid | 71.1 |
| C18:2 Linoleic Acid | 7.66 |
| C18:3 Linoleic Acid | 0.71 |

M/P Ratio (Monosaturated Fats/Polysaturated Fats): 6.2
Polyphenols (ppm Catteic Acid): 0.25
K225 (Bitterness): 0.0125

What is claimed is:

1. A new distinct olive plant as described and illustrated that is characterized by having the general characteristics of the 'Arbequina Standard' variety but is distinguished therefrom in that it has higher productivity, larger fruit size, better pulp to stone ratio, and higher oil yield, the plants being ideally suited for mechanical harvesting and high density planting, with the fruit maturing in northern California in about the first week of October.

* * * * *